(12) United States Patent
Coleman

(10) Patent No.: US 8,945,099 B2
(45) Date of Patent: Feb. 3, 2015

(54) SHAFT ROTATING DEVICE AND MEDICAL INSTRUMENT WITH SUCH A DEVICE

(75) Inventor: Stuart Coleman, Dundee (GB)

(73) Assignee: University of Dundee (GB)

( * ) Notice: Subject to any disclaimer, the term of this patent is extended or adjusted under 35 U.S.C. 154(b) by 176 days.

(21) Appl. No.: 13/599,352

(22) Filed: Aug. 30, 2012

(65) Prior Publication Data
US 2013/0053836 A1   Feb. 28, 2013

(30) Foreign Application Priority Data

Aug. 30, 2011   (EP) .................................... 11179400

(51) Int. Cl.
*A61B 17/00* (2006.01)
*A61B 17/29* (2006.01)
(52) U.S. Cl.
CPC .......... *A61B 17/29* (2013.01); *A61B 2017/2927* (2013.01)
USPC ........................................................ 606/1
(58) Field of Classification Search
CPC ........... A61B 17/2804; A61B 17/2909; A61B 2017/2903; A61B 2017/2929; A61B 2017/291; A61B 2017/293
USPC .................................................... 606/1, 205
See application file for complete search history.

(56) References Cited

U.S. PATENT DOCUMENTS

| 3,967,831 | A | * | 7/1976 | Chang et al. ................. 279/23.1 |
| 4,657,425 | A | * | 4/1987 | Takahashi ...................... 403/104 |
| 5,098,241 | A | * | 3/1992 | Aldridge et al. .............. 411/433 |
| 5,275,614 | A | | 1/1994 | Haber et al. |
| 2009/0177039 | A1 | * | 7/2009 | Frank ............................. 600/137 |
| 2010/0193568 | A1 | | 8/2010 | Scheib et al. |

FOREIGN PATENT DOCUMENTS

EP   2077094 A1   7/2009

* cited by examiner

*Primary Examiner* — Lynsey Crandall
*Assistant Examiner* — Nathan J Jenness
(74) *Attorney, Agent, or Firm* — St. Onge Steward Johnston & Reens LLC

(57) ABSTRACT

A medical instrument including a shaft rotating device for rotating a shaft of a medical instrument about its longitudinal axis relative to a handle of the medical instrument The shaft rotating device includes a operating element arranged at a proximal portion of the shaft such that the shaft is rotatable relative to the handle against frictional forces. The shaft rotating device includes a coil spring arrangement having a surface and being in frictional contact with a surface of a counterpart for keeping the shaft and the handle rotationally stationary with respect to each other and movable against frictional forces. The operating element is operatively connected with the coil spring arrangement such that torque applied to the operating element decreases the frictional forces, while the shaft and coil spring arrangement are operatively connected such that torque applied to a distal portion of the shaft increases the frictional forces.

5 Claims, 3 Drawing Sheets

SHAFT ROTATING DEVICE AND MEDICAL INSTRUMENT WITH SUCH A DEVICE

CROSS REFERENCE TO RELATED APPLICATION

This application claims priority from European patent application 11179400.4, filed on Aug. 30, 2011. The entire contents of this priority application is incorporated herein by reference.

BACKGROUND OF THE INVENTION

The invention relates to a shaft rotating device for rotating a shaft of a medical instrument about its longitudinal axis relative to a handle of the medical instrument.

The invention further relates to a medical instrument for endoscopic surgery, comprising a shaft and a handle, wherein the handle is arranged at a proximal portion of the shaft.

A shaft rotating device and a medical instrument are known from EP 2 077 094 A1.

The known medical instrument comprises an elongated shaft, at whose proximal portion a handle is arranged. A distal portion of the shaft is used to introduce pivotably arranged jaws into a cavity of a patient during an operation for grasping and/or cutting tissue. At least one jaw is in driving connection with the handle via a thin pull/push rod for controlling its grasping and/or cutting action. At the proximal portion of the shaft a shaft rotating device is arranged, which allows for rotating the shaft about its longitudinal axis relative to the handle and against frictional forces exerted between a surface of a frictional element comprising two coil springs wound counter-directionally around a surface of a counterpart which is connected with the handle.

This arrangement of the frictional element on the one hand and the counterpart on the other hand provides the frictional forces, such that the shaft and the handle are rotationally stationary with respect to each other, when no forces are applied to the operating element. In addition, when applying a torque to the operating element, the frictional forces are decreased such that the shaft is easily rotatable relative to the handle without increased physical effort. In contrast, applying a torque to the distal portion of the shaft results in an increase of the frictional forces such that the shaft and the handle are rotationally fixed to each other. Thereby, it is ensured that the jaw parts do not change their rotational orientation when torques are exerted on the jaw parts during the grasping and/or cutting action.

In the known shaft rotating device, two coil springs wound counter-directionally with respect to one another are used to achieve both, a decrease of the frictional forces when a torque is applied to the operating element and an increase of frictional forces when a torque is applied to the distal portion of the shaft.

Thus, the known shaft rotating device has the drawback, that the frictional element, comprising two coil springs which require relatively large space, is complex and cost intensive in terms of manufacturing expenditure.

Furthermore, it is a disadvantage that a rotation transmission element of the shaft rotating device which is arranged between the operating element and the coil spring arrangement, comprises a complex arrangement of at least three separated grooves in which the end portions of the two counter-directionally wound coil springs engage. This complex design also causes an increased effort during manufacturing accompanied by increased production costs and increased effort in assembling and disassembling the device.

SUMMARY OF THE INVENTION

It is an object of the present invention to improve a shaft rotating device such that the shaft rotating device is less complex and less expensive and requires less space.

It is another object of the invention to provide an improved medical instrument with such a shaft rotating device.

According to an aspect, a shaft rotating device for rotating a shaft of a medical instrument about its longitudinal axis relative to a handle of the medical instrument is provided, comprising a shaft having a proximal portion, a distal portion, and a longitudinal axis, a handle arranged at the proximal portion of the shaft, an operating element for rotating the shaft, which is arranged at the proximal portion of the shaft and which is in driving connection with the shaft such that the shaft is rotatable relative to the handle against frictional forces, a coil spring arrangement having a first surface, a first end portion and a second end portion, and having windings between the first end portion and the second end portion, a counterpart, fixed with respect to the handle, and having a second surface, said windings wound around the second surface of the counterpart, wherein all the windings of the coil spring arrangement are wound in a unique winding sense around the second surface of the counterpart, for keeping the shaft and the handle rotationally stationary with respect to each other and movable against the frictional forces exerted between the first surface of the coil spring arrangement and the second surface of the counterpart, the operating element being operatively connected with the coil spring arrangement such that a torque applied to the operating element decreases the frictional forces, and wherein the shaft and the coil spring arrangement are operatively connected with one another such that a torque applied to the distal portion of the shaft increases the frictional forces.

An advantage of the new shaft rotating device of the medical instrument based on the invention described is that it comprises a coil spring arrangement whose windings are wound around the surface of a counterpart in a unique winding sense being in frictional contact with the surface of the counterpart. Such a coil spring arrangement allows the use of a single spring only. Two end portions, forming a first end and a second end of the single spring, allow a simple operational connection to the operating element. Here, the operational connection between the end portions of the spring and the operating element can be accomplished in mechanically simple fashion by sidewalls and a bottom wall of a single, substantially rectangular groove oriented substantially parallel to the longitudinal axis of the shaft.

In addition, according to a refinement of the invention, the operational connection between the end portions of the spring and a rotation transmission element can be accomplished by edges of a single slit of the rotation transmission element which is orientated substantially parallel to the longitudinal axis of the shaft. Within this refinement it is apparent that the necessity of only one groove to connect the end portions of the single spring with the operating element and only one slit of the rotation transmission element through which the end portions of the spring pass for operatively connecting the spring with the rotation transmission element facilitates the manufacturing process leading to a less expensive production as an advantage on the manufacturer side and a less complex device leading to a simplification of assembling and disassembling the device as an advantage for the customer.

Based on the optional refinement to use one spring only as discussed before, the coil spring arrangement can be designed by a single spring with only one or a little number of windings, which fulfils all necessary functional requirements and leads to a more compact device being less expensive in production.

In a preferred refinement of the invention the coil spring arrangement consists of one spring only.

Providing the frictional forces between the shaft and the handle by one spring only is advantageous as no further technical means are required for decreasing or increasing the frictional forces. Therefore, production costs of the shaft rotating device, and thus the medical instrument are advantageously lower compared to the known shaft rotating device.

In a further preferred refinement of the invention the first end portion and the second end portion of the coil spring arrangement engage into a single groove of the operating element.

The operating element is in direct operative connection with the end portions of the coil spring arrangement via the groove, providing an effective rotation of the shaft when the operating element is rotated. In addition, in a simple configuration, the groove may have a substantially rectangular profile and extend continuously parallel to the longitudinal axis of the shaft which arrangement further reduces the manufacturing expenditure of the shaft rotating device.

In a further preferred refinement of the invention, a rotation transmission element is circumferentially arranged between the operating element and the coil spring arrangement, and has a single slit oriented in a direction substantially parallel to the longitudinal axis of the shaft.

The rotation transmission element comprising one slit only, on the one hand enables an efficient suppression of shaft rotation caused by torque applied to the distal portion of the shaft, and on the other hand decreases the manufacturing expenditure compared to the known shaft rotating device having a rotation transmission element with two slits and one groove.

In a further preferred refinement of the invention, the first end portion and the second end portion of the coil spring arrangement engage through the slit of the rotation transmission element into the groove of the operating element.

Here, the arrangement of the end portions of the coil spring arrangement relative to the rotation transmission element and the operating element ensures that the shaft is rotatable clock and anti-clockwise. Moreover, the design used, given by a single slit within the rotation transmission element as a guide-through and a single groove within the operating element as a mount for the end portions of the coil spring arrangement, is very simple in terms of manufacturing.

In a further preferred refinement of the invention longitudinal edges of the slit of the rotation transmission element are slightly spaced apart from the first end portion and the second end portion of the coil spring arrangement.

Here, the edges of the slit of the rotation transmission element come into engagement with one of the first or second end portions of the coil spring arrangement, thereby decreasing the diameter of the coil spring arrangement, when torque is exerted on the distal portion of the shaft, leading to an increase of the frictional forces between the counterpart and the coil spring arrangement, whereby a shaft rotation is suppressed. On the other hand, when the operating element is rotated, the slight distance between the first and second end of the slit of the rotation transmission element allows for an increase of the diameter of the coil spring arrangement, thus lowering the frictional forces between the windings of the coil spring arrangement and the counterpart, thus enabling the shaft to freely rotate relative to the handle.

In a further preferred refinement of the invention, the rotation transmission element has an inner diameter larger than an outer diameter of the coil spring arrangement.

This advantageous refinement guarantees that no further frictional forces are provided between the rotation transmission element and the frictional element, which could block the movement of the shaft relative to the handle when rotation of the shaft relative to the handle is required. In addition, a damage of both, the rotation transmission element, and the frictional element due to frictional wear are prevented, saving repairing costs for the shaft rotating device and the medical instrument.

Further, according to another aspect, a medical instrument for endoscopic surgery is provided, comprising a shaft having a proximal portion, a distal portion, and a longitudinal axis, a handle arranged at the proximal portion of the shaft, a shaft rotating device, the shaft rotating device comprising: an operating element for rotating the shaft, which is arranged at the proximal portion of the shaft and which is in driving connection with the shaft such that the shaft is rotatable relative to the handle against frictional forces, a coil spring arrangement having a first surface, a first end portion and a second end portion, and having windings between the first end portion and the second end portion, a counterpart, fixed with respect to the handle, and having a second surface, said windings wound around the second surface of the counterpart, wherein all the windings of the coil spring arrangement are wound in a unique winding sense around the second surface of the counterpart, for keeping the shaft and the handle rotationally stationary with respect to each other and movable against the frictional forces exerted between the first surface of the coil spring arrangement and the second surface of the counterpart, the operating element being operatively connected with the coil spring arrangement such that a torque applied to the operating element decreases the frictional forces, and wherein the shaft and the coil spring arrangement are operatively connected with one another such that a torque applied to the distal portion of the shaft increases the frictional forces.

Further advantages will become apparent from the following description and the accompanying drawings. It is to be understood that the afore-mentioned features and those to be explained below are not only applicable in the combination given, but also in other combinations or in isolation without departing from the scope of the invention.

BRIEF DESCRIPTION OF THE DRAWINGS

An exemplary embodiment of the invention is illustrated in the drawings and will be described herein after with reference thereto. In the drawings.

DESCRIPTION OF AN EXEMPLARY PREFERRED EMBODIMENT

Figure 1:
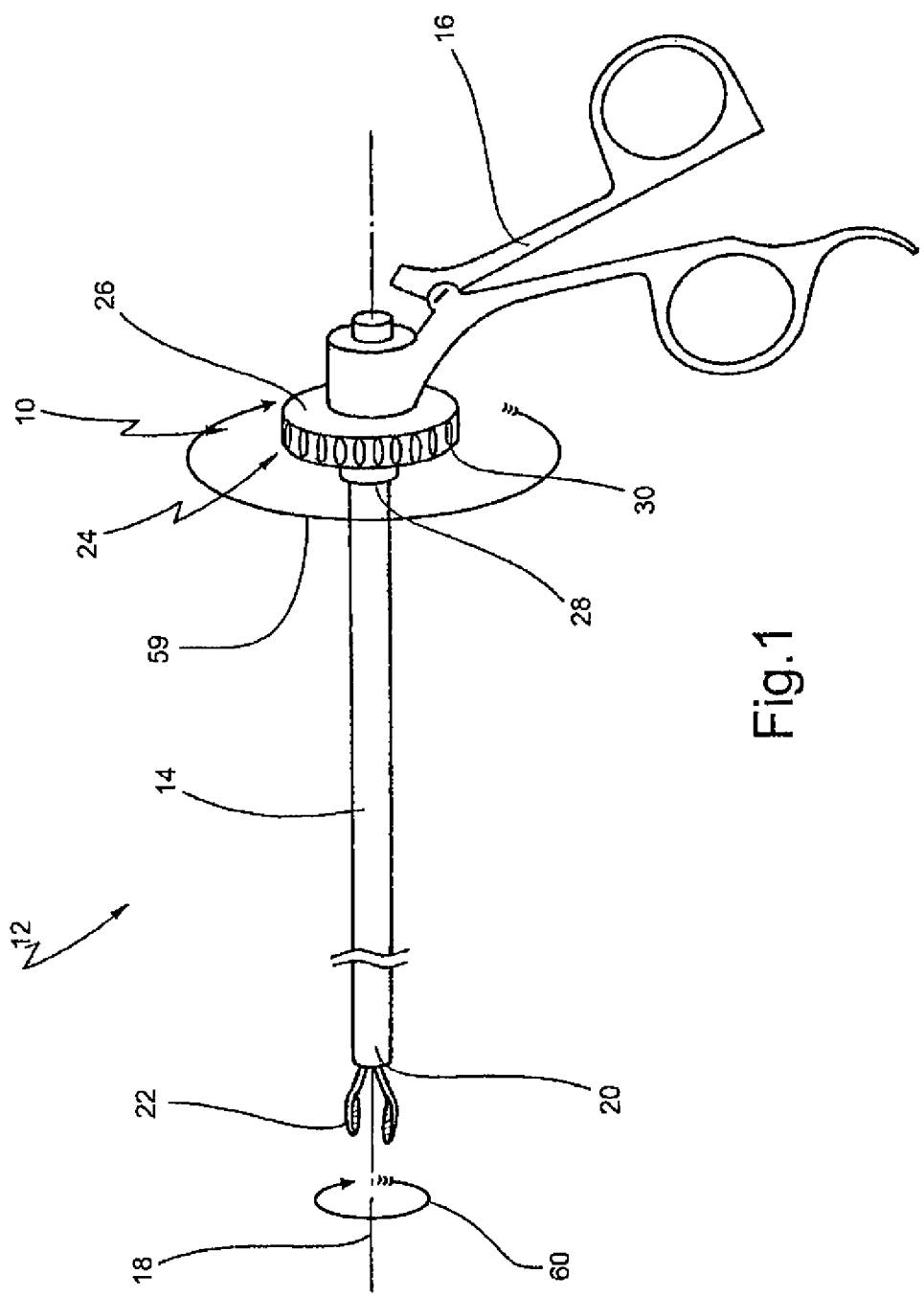
FIG. 1 shows a medical instrument comprising a shaft rotating device in accordance with the invention.

FIG. 1 shows, in a schematic representation, a shaft rotating device generally labelled with reference numeral 10 as part of a medical instrument 12. The shaft rotating device 10 is used for rotating an elongated hollow shaft 14 of the medical instrument 12 with respect to a handle 16 of the medical instrument 12 about a longitudinal axis 18 of the shaft 14. Further details of the shaft rotating device 10 are shown in FIGS. 2 and 3.

During a medical surgery a distal portion 20 of the shaft 14 is introduced into a body cavity of a patient for grasping and/or cutting tissue. To this end, jaws 22, being pivotably arranged at the distal portion 20 of the shaft 14, are operatively connected with the handle 16 via an axially movable force transmission element 23 which can be a push/pull rod for actuating the jaws. By rotating the shaft 14 relative to the handle 16, the jaws 22 are rotated as well in order to obtain the most convenient position of the jaws 22 with respect to the tissue and thus improving their grasping and/or cutting capabilities during the surgery.

The shaft rotating device 10 comprises an operating element 24 configured as a rotating wheel 26, for rotating the shaft 14 relative to the handle 16. The rotating wheel 26 is arranged at a proximal portion 28 of the shaft 14. Moreover, it is in driving connection with the shaft 14 such that the shaft 14 is rotatable relative to the handle 16 against frictional forces. The arrangement of the rotating wheel 26 allows for rotating the shaft 14 clock and anti-clockwise by an angular range of 360°. The rotating wheel 26 comprises notches 30 oriented parallel with respect to the longitudinal axis 18 of the shaft 14, facilitating its usage and decreasing the danger of slipping off the rotating wheel 26.

Figure 2:
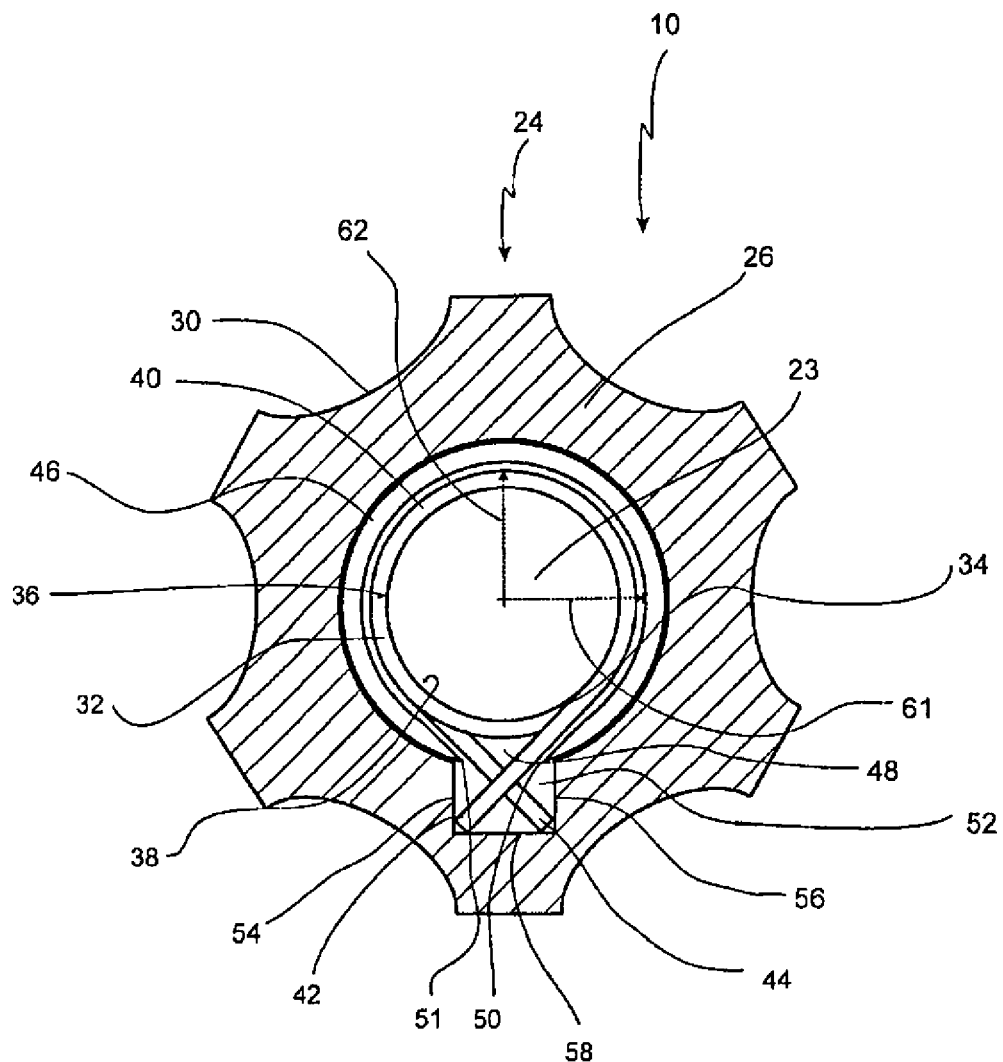
FIG. 2 shows a view of the shaft rotating device in a partial cross-section perpendicular to the longitudinal axis of the shaft, showing a rotating wheel, a rotation transmission element and a coil spring arrangement of the shaft rotating device.
Figure 3:
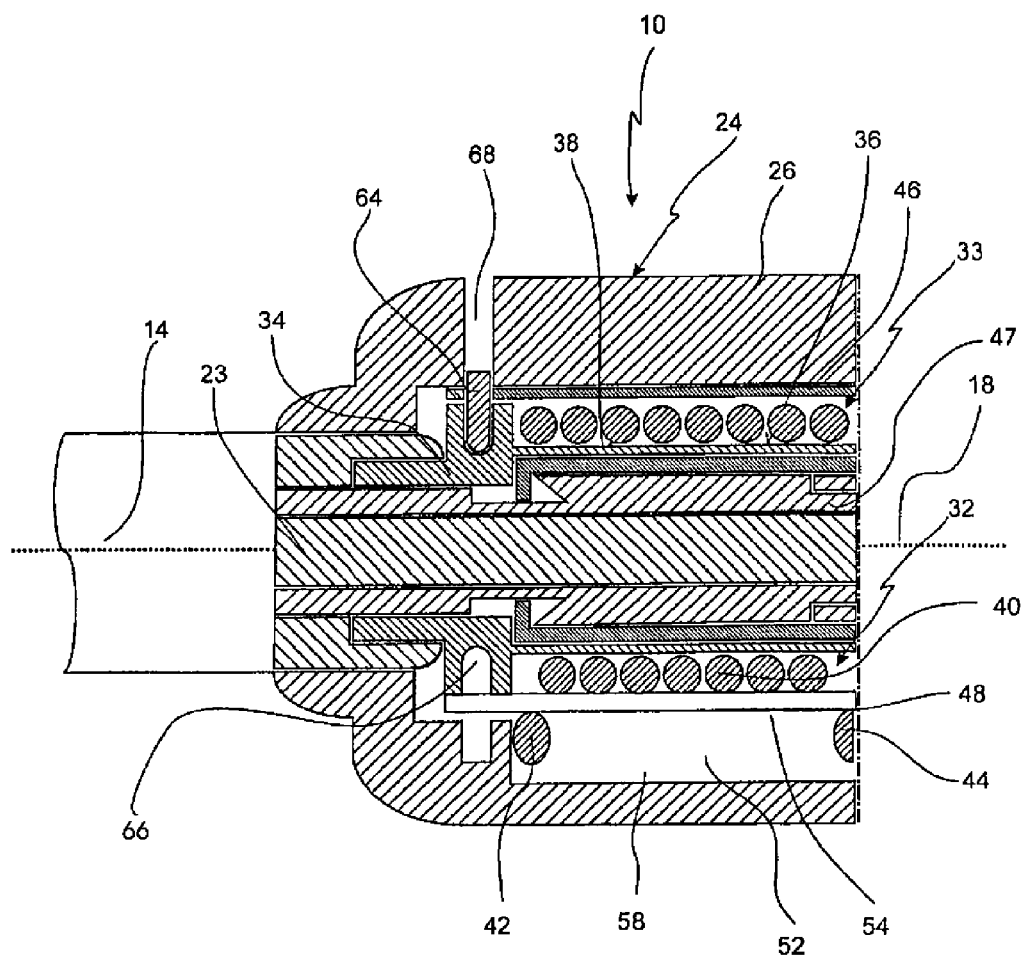
FIG. 3 shows a longitudinal section of a portion of the shaft rotating device.

As shown in FIG. 2 and FIG. 3, the shaft rotating device 10 further comprises a coil spring arrangement 32 and a counterpart 34. The counterpart 34 comprises a surface 36 which is in frictional connection with a surface 38 of the coil spring arrangement 32, which consists of one spring 33 only. The coil spring arrangement 32 has windings 40 which are wound in a unique winding sense around the surface 36 of the counterpart 34. In the present embodiment, there are shown eight windings 40, but it is considerable to provide less or more windings 40. The coil spring arrangement 32 has a first end portion 42 on one longitudinal end and a second end portion 44 on the other longitudinal end. Furthermore, the shaft rotating device 10 comprises a rotation transmission element 46 which is rotationally fixed connected to the proximal portion 28 of the shaft 14. Furthermore, a shaft extension element 47 being circumferentially arranged between the rotation transmission element 46 and the force transmission element 23, is rotationally fixedly connected to the shaft 14 and rotationally fixedly connected to the rotation transmission element 46. The rotation transmission element 46 is circumferentially arranged between the operating element 24 and the coil spring arrangement 32. It comprises a slit 48 oriented in a direction substantially parallel to the longitudinal axis 18 of the shaft 14. The slit 48 of the rotation transmission element 34 defines edges 50 and 51, which are slightly spaced apart from the first and second end portion 42 and 44 of the coil spring arrangement 32.

Moreover, the first end portion 42 and the second end portion 44 of the coil spring arrangement 32 engage through the slit 48 of the rotation transmission element 46 and into a groove 52 of the operating element 24. The groove 52 has a profile of substantially rectangular shape and is oriented substantially parallel to the longitudinal axis 18 of the shaft 14. The groove 52 has a first sidewall 54, a second sidewall 56 and a bottom wall 58, which support the first end portion 42 and the second end portion 44 of the coil spring arrangement 32 such that the windings 40 of the coil spring arrangement 32 are slightly squeezed in order to provide frictional forces between them and the counterpart 34 which frictional forces can be decreased and increased as will be described later.

The handle 16 is rotationally fixedly connected to the counterpart 34. The counterpart 34 is in frictional connection with the coil spring arrangement 32. The coil spring arrangement 32 is operatively connected to the rotation transmission element 46, which in turn is rotationally fixedly connected to the shaft 14 and the operating element 24.

If no torque 60 is applied to the distal portion 20 of the shaft 14, and if the operating element 24 is not rotated, the frictional forces between the coil spring arrangement 32 and the counterpart 34 are sufficient for keeping both, the handle 16 and the shaft 14 rotationally stationary with respect to each other.

The coil spring arrangement 32 and the rotating wheel 26 are operationally connected with respect to one another such that a torque 59 externally applied to the rotating wheel 26 decreases the frictional forces between the surface 38 of the coil spring arrangement 32 and the surface 36 of the counterpart 34. This is accomplished as follows. If the rotating wheel 26 in FIG. 2 is rotated in a clockwise direction, the sidewall 56 of the groove 52 of the rotating wheel 26 pushes the end portion 44 of the coil spring arrangement 32 to the left whereby the diameter of the windings 40 is increased, thus lowering the frictional forces between the coil spring arrangement 32 and the counterpart 34. This increase of the diameter is rendered possible by the slight distance of the end portions 42 and 44 from the edges 50, 51 of the slit 48 of the rotation transmission element 46. If the rotating wheel 26 is rotated in counter-clockwise direction in FIG. 2, the sidewall 54 pushes the end portion 42 of the coil spring arrangement 32 to the right, also leading to an increase of the diameter of the coil spring arrangement 32 and thus lowering the frictional forces between the coil spring arrangement 32 and the counterpart 34. Thus, by rotating the rotating wheel 26 in clockwise or counter-clockwise direction, the shaft 14 can easily be rotated.

In contrast, the frictional forces exerted between both components are increased for rotationally fixing the shaft 14 with respect to the handle 16, if the torque 60 is applied to the distal portion 20 of the shaft 14. For instance, this situation typically appears during the surgery when the jaws 22 interact with the tissue. In order to suppress the rotation of the shaft 14 in this case, one of the edges 50 or 51 of the slit 48 of the rotation transmission element 46, depending on the direction of the torque, comes into contact with the first end portion 42 or the second end portion 44, and pushes the first end portion 42 to the right or the second end portion 44 to the left of FIG. 2, whereby the diameter of the windings 40 is decreased and the frictional forces between the windings 40 and the counterpart 34 are increased.

Thus, the arrangement of the components mentioned before guarantees, that a rotation of the shaft 14 caused by the external torque 60 exerted to the distal portion 20 of the shaft 14 is suppressed while a rotation of the shaft 14 caused by a torque 59 applied to the operating element 24 is assured.

The arrangement of the two end portions 42, 44 of the coil spring arrangement 32 relative to the rotation transmission element 46 and the slit 48 of the rotation transmission element 46, where the two end portions 42 and 44 pass through, and the operating element 24 with the groove 52 where the end portions 42, 44 are mounted in, ensures that the shaft 14 is rotatable clock- and anticlockwise.

Moreover, as the edges 50 of the slit 48 are slightly separated from the first end portion 42 and the second end portion 44 of the coil spring arrangement 32 ensures both independently, a suppression of shaft rotation caused by a torque 60 exerted on the distal portion 20 and a rotation of the shaft 14 caused by a torque 59 exerted on the operating element 24.

The rotation transmission element 46 has an inner diameter 61 being slightly larger than an outer diameter 62 of the coil spring arrangement 32. Therefore, no additional frictional forces are exerted between these two components in any operating state of the device, allowing for a simple handling and additionally preventing frictional wear of the coil spring arrangement 32 and/or the rotation transmission element 46.

FIG. 3 in detail shows that the groove 52 in the operating element 24 is oriented substantially parallel to the longitudinal axis 18 of the shaft 14 in continuous fashion.

Furthermore, the shaft rotating device 10 further comprises a fastening bolt 64 engaging into a circumferential groove 66 which is part of the counterpart 34 being fixedly connected to the handle 16. The fastening bolt 64 engages through a hole guidance 68 into the circumferential groove 66. The hole guidance 68 is oriented substantially perpendicular to the longitudinal axis 18 of the shaft 14 and passes through the rotating wheel 26. The fastening bolt 64 provides an axial fixing of the components of the device 10, but allows for rotational movement as described above.

What is claimed is:

1. A medical instrument for endoscopic surgery, comprising:
    a shaft having a proximal portion, a distal portion, and a longitudinal axis;
    a handle arranged at the proximal portion of the shaft;
    a shaft rotating device, the shaft rotating device comprising:
        an operating element for rotating the shaft, which is arranged at the proximal portion of the shaft and which is in driving connection with the shaft such that the shaft is rotatable relative to the handle against frictional forces;
        a coil spring arrangement having a first surface, a first end portion and a second end portion, and having windings between the first end portion and the second end portion, wherein the coil spring arrangement is a single spring and the first end portion and the second end portion of the coil spring arrangement engage into a single groove of the operating element;
        a counterpart, fixed with respect to the handle, and having a second surface, said windings wound around the second surface of the counterpart, wherein all the windings of the coil spring arrangement are wound in a same winding sense around the second surface of the counterpart, for keeping the shaft and the handle rotationally stationary with respect to each other and movable against the frictional forces exerted between the first surface of the coil spring arrangement and the second surface of the counterpart;
        the operating element being operatively connected with the coil spring arrangement such that a torque applied to the operating element decreases the frictional forces, and wherein the shaft and the coil spring arrangement are operatively connected with one another such that a torque applied to the distal portion of the shaft increases the frictional forces.

2. The medical instrument of claim 1, further comprising a rotation transmission element, circumferentially arranged between the operating element and the coil spring arrangement, the rotation transmission element having a single slit, oriented in a direction parallel to the longitudinal axis of the shaft.

3. The medical instrument of claim 2, wherein the first end portion and the second end portion of the coil spring arrangement engage through the slit of the rotation transmission element into the groove of the operating element.

4. The medical instrument of claim 2, wherein the slit has longitudinal edges which are spaced apart from the first end portion and the second end portion of the coil spring arrangement.

5. The medical instrument of claim 2, wherein the rotation transmission element has an inner diameter larger than an outer diameter of the coil spring arrangement.

* * * * *